United States Patent [19]

Strecker et al.

[11] 4,291,012

[45] Sep. 22, 1981

[54] TECHNETIUM-LABELLED DIAGNOSTIC AGENT FOR THE EXAMINATION OF THE RES

[75] Inventors: Helmut Strecker, Seeheim-Jugenheim; Michael Molter, Frankfurt am Main; Gerhard Kloss, Kelkheim; Eberhard Schickel, Selters, all of Fed. Rep. of Germany

[73] Assignee: Hoechst Aktiengesellschaft, Frankfurt am Main, Fed. Rep. of Germany

[21] Appl. No.: 908

[22] Filed: Jan. 4, 1979

[30] Foreign Application Priority Data

Jan. 7, 1978 [DE] Fed. Rep. of Germany ....... 2800538

[51] Int. Cl.$^3$ ..................... A61K 49/00; A61K 43/00; G01T 1/00
[52] U.S. Cl. ........................................ 424/1; 128/659; 424/1.5; 424/9
[58] Field of Search ........................... 424/1.9; 128/659

[56] References Cited

U.S. PATENT DOCUMENTS

| | | | |
|---|---|---|---|
| 3,743,713 | 7/1973 | Kato et al. | 424/1 |
| 4,066,742 | 1/1978 | Garrett | 424/1 |
| 4,087,516 | 5/1978 | Laidler et al. | 424/1 |

Primary Examiner—Brooks H. Hunt
Assistant Examiner—Christine M. Nucker
Attorney, Agent, or Firm—Curtis, Morris & Safford

[57] ABSTRACT

A process is disclosed for the preparation of a diagnositc agent for scanning the RES, in particular the liver, by mixing the sodium salt of 1-phenyl-2,3-dimethyl-pyrazolone-4-methylamino-methylsulfonic acid or 1-phenyl-2,3-dimethyl-pyrazolone in aqueous solution with tin(II) salt, adjusting the solution to a pH between 4 and 9, optionally lyophilizing the mixture and adding $^{99m}$Tc-pertechnetate in physiological saline solution.

7 Claims, No Drawings

TECHNETIUM-LABELLED DIAGNOSTIC AGENT FOR THE EXAMINATION OF THE RES

The present invention relates to a $^{99m}$technetium-labelled diagnostic agent for the examination of the RES.

$^{99m}$Technetium is useful in the nuclear-medical field for diagnostic applications owing to its favorable radiation energy of 140 keV, its relatively short half-life of 6 hours and the lack of corpuscular radiation. In order to avoid great losses of radioactivity by decay during the transport $^{99m}$Tc is generally produced in the hospital in a so-called nuclide generator (as described for example in German Offenlegungsschrift No. 2,236,565).

$^{99m}$Tc obtained in this nuclide generator, which is present at NaTcO$_4$ in a 0.9% NaCl solution, can be used as such for medical diagnostic only to a limited extent, mainly for the scintography of the brain, the thyroid and the stomach. For other examinations suitable organ-specific carrier substances for $^{99m}$Tc must be "labelled" with this radionuclide. Suitable carrier substances include for example particles of different size for the liver and lung diagnostic and pyrophosphate for skeletal scanning.

These carrier substance are labelled after reduction of $^{99m}$Tc which is initially present in the form of the rather inert pertechnetate to a reactive lower degree of oxidation (probably degree 4 or 5). The reduction may be carried out in an acid medium, using for example thiosulfate, in a neutral medium using mainly tin(II) or in electrolytical manner. In the first case the reaction solution must be neutralized prior to injection. This process results in a so-called "multi-component kit" (see below). The electrolytical reaction requires a high display on apparatus.

$^{99m}$Technetium is labelled in the hospital in order to avoid losses of radioactivity due to decay. For this purpose a simple, rapid and safe process should be employed. Since the preparation is for injection, it must be sterile, pyrogen-free and non-toxic. Labelling kits are being used to an increasing extent. Such a kit consists of a device and inactive substances adjusted to each other which are afterwards combined with the nuclide generator product to give an organ-specific diagnostic agent. Especially easy to handle as a labelling kit is a so-called "labelling unit" (single component kit), which consists of a vial containing the combination of substances, into which the product of the generator is injected by means of a syringe in order to provide the diagnostic agent ready for injection.

Labelling units of the above type frequently consist of a combination of an organ-specific carrier substance and a tin(II) salt.

Known substances and kits for the diagnostic of the RES (liver, spleen and bone marrow) are, for example:
1. Colloidal 198-gold,
2. Colloidal $^{99m}$Tc-sulfur,
3. $^{99m}$Tc-tin hydroxide,
4. $^{99m}$Tc-tin phytate,
5. $^{113m}$Indium iron hydroxide.

Processes using these substances have the following disadvantages:

Colloidal 198-gold is distinguished by a homogeneous particle size. However, the use of 198-gold involves an undesired high strain by radiation of the patient to be examined to the unfavorable radiation properties of this substance (half-life 2.7 days, corpuscular radiation) as compared to $^{99m}$Tc.

Colloidal $^{99m}$Tc-sulfur is an appropriate preparation for diagnostical application, however, it is obtained in a relatively complicated process, in which the eluate must be acidified, supplemented with thiosulfate, boiled and finally neutralized. This involves an increased radiation exposure of the staff.

When preparing a colloid merely consisting of tin hydroxide particles, aggregation of the particles will occur soon, (ageing process). In this case, a colloid useful for injection is not obtained after the addition of the pertechnetate solution. A further disadvantage is that the relatively great particle aggregates concentrate in the lung.

$^{99m}$Tc-phytate can likewise be prepared in simple manner from a labelling unit. However, the principle is not yet known according to which the preparation is concentrated in the liver. Probably the phytate reacts with the calcium ions of the blood after intravenous injection with the formation of particles. The quality of the particles depends on variable parameters, for example the calcium content of the blood and the injection velocity so that the behavior of the preparation and thus the diagnostic statements vary.

$^{113m}$Indium iron hydroxide particles have disadvantages as regards their physiological behavior and the high radiation energy of $^{113m}$indium which are not very suitable for examinations with the γ-camera.

The present invention provides a process for the preparation of a diagnostic agent for the liver, that does not show the disadvantages of the above diagnostic agents.

The present invention relates to a process for the preparation of a diagnostic agent for visualizing the RES, in particular the liver, which comprises mixing the sodium salt of 1-phenyl-2,3-dimethyl-pyrazolone-4-methylamino-methylsulfonic acid (A) or 1-phenyl-2,3-dimethyl-pyrazolone (B) in an aqueous solution with tin(II) salt in a molar ratio of 15:1 to 110:1, adjusting the resulting solution to a pH between 4 and 9, preferably between 5.5 and 6.5, optionally lyophilizing it and, afterwards, depending on the intended application, adding from 0.1 to 100 mCi of $^{99m}$Tc-pertechnetate in 1 to 10 ml of physiological saline solution.

The concentrations of (A) or (B) are advantageously in the range from 0.1 to 200 mg/ml, preferably in the range from 1 to 50 mg/ml.

To prepare the diagnostic agent, a solution of (A) or (B) is suitably mixed with the tin(II) salt solution having a pH below 2, preferably between 1 and 1.5. Subsequently the mixture is adjusted to a pH between 4 and 9, preferably between 5.5 and 6.5, by the addition of alkali metal hydroxide solution while stirring. In the beginning, the solution is clear. Starting from a pH of approximately 3.5, the solution becomes turbid due to the formation of tin-(A) or tin-(B) particles.

The diagnostic agent according to the invention is not merely a mixture of tin(II) salt with compound (A) or (B), which can be clearly seen by comparing the properties of the individual components and of the mixtures upon modification of the pH. Aqueous solutions of (A) or (B) are clear in a pH range of from 2 to 11.5. Solutions of tin(II) salt with or without compound (A) or (B), which are altogether clear at low pH values, begin to become turbid from a pH of 3.5, the turbidity being at maximum at a pH of about 4.5. Solutions containing only tin(II) salt clear up at a pH above 8.5, whereas solutions containing tin(II) salt and compound (A) or tin(II) salt and compound (B) remain turbid up to pH values above 11.

The particle suspensions are either used within 24 hours or for stabilization purposes lyophilized at a temperature below 0° C., preferably between −5° and −20° C., under a pressure below 2 torrs, preferably between 0.2 and 0.01 torr, and subsequently protected by an inert gas, for example nitrogen.

The present invention further relates to a diagnostic agent for visualizing the RES, in particular the liver, which comprises colloidal (A) or (B) -tin-$^{99m}$Tc compounds in physiological saline solution.

The following examples illustrate the invention:

EXAMPLE 1

1 g of (A) is dissolved in about 800 ml of bidistilled water. Thereafter 20 mg $SnCl_2 \cdot 2 H_2O$ are dissolved in 1 ml 0.1 n HCl and added to the solution of (A). The components are mixed, the mixture is adjusted to a pH of 6.0 by adding NaOH with stirring, and the volume of the batch is adjusted to 100 ml by adding bidistilled water. If required, the pH is corrected.

The final solution is divided into 1 ml portions. For labelling, 0.1 to 100 mCi, preferably 2 to 20 mCi, of $^{99m}TcO_4$ in 1 to 10 ml of physiological saline solution is added. The diagnostic agent should be used within 24 hours.

All of the solutions employed are flushed with nitrogen to be free of oxygen. The preparation of the solutions and the separation into individual portions are also performed with the exclusion of oxygen. For preparing solutions for use in humans, sterile and pyrogen-free substances and solvents are used.

(A) = the sodium salt of 1-phenyl- 2,3-dimethyl-pyrazolone-4-methyl-amino-methylsulfonic acid.

EXAMPLE 2

5 g pf (B) are dissolved in about 900 ml of bidistilled water and 200 mg $SnCl_2 \cdot 2 H_2O$ in 2 ml 0.1 n HCl are added. After mixing the components, the solution is adjusted to a pH of 6.0 by adding alkali metal hydroxide solution, for example NaOH while stirring. The volume of the solution is adjusted to 1,000 ml by adding further quantities of bidistilled water. The batch is stirred for 2 hours with the exclusion of oxygen. The suspension thus obtained is subsequently divided into 1 ml portions to be filled in injection bottles prefrozen with liquid nitrogen.

The thus frozen portions are lyophilized without intermediate melting on a plate having a temperature of −10° C. and under a pressure of <0.1 torr. After having completely dried the portions, the injection vials are filled with nitrogen and closed. In this way a package unit (labelling unit) suitable for labelling by means of $^{99m}Tc$ is obtained.

Depending on the intended application, from 0.1 to 100 mCi, preferably 2 to 20 mCi, of $^{99m}TcO_4$ in 1 to 10 ml of physiological saline solution, are added to a labelling unit, prior to use. The resulting ready for use diagnostic agent should be applied within 24 hours.

All of the used solution are flushed with nitrogen to be oxygen-free. The preparations of the solution and its separation into individual portions are performed with the exclusion of oxygen. For use in humans the solutions are sterile and pyrogen-free, since they are prepared from sterile substances and solvents.

(B) = 1-phenyl-2,3-dimethyl-pyrazolone.

We claim:

1. A process for the preparation of a diagnostic agent for scanning the RES, which comprises mixing the sodium salt of 1-phenyl-2,3-dimethyl-pyrazolone-4-methylamino-methylsulfonic acid or 1-phenyl-2,3-dimethyl-pyrazolone in an aqueous solution with tin(II) salt in a molar ratio of 15:1 to 110:1, adjusting the resulting solution to a pH between 4 and 9, and afterwards adding from 0.1 to 100 mCi of $^{99m}Tc$-pertechnetate in 1 to 10 ml of physiological saline solution.

2. The process as defined in claim 1 wherein the pH adjusted mixture of sodium salt of 1-phenyl-2,3-dimethyl-pyrazolone-4-methylamino-methylsulfonic acid and 1-phenyl-2,3-dimethyl-pyrazolone with tin(II) salt is further lyophilized.

3. A process as defined in claim 8 wherein the concentration of 1-phenyl-2,3-dimethyl-pyrazolone-4-methylaminomethylsulfonic acid or 1-phenyl-2,3-dimethyl-pyrazolone is in the range of from 0.1 to 200 mg/ml.

4. A process as claimed in claim 1 or 3 wherein the concentration of 1-phenyl-2,3-dimethyl-pyrazolone-4-methylamino-methylsulfonic acid or 1-phenyl-2,3-dimethyl-pyrazolone is in the range of from 1 to 50 mg/ml.

5. A process as claimed in claim 1 or 3 which comprises reacting a mixture consisting essentially from 1 to 50 mg of 1-phenyl-2,3-dimethyl-pyrazolone-4-methylaminomethylsulfonic acid or 1-phenyl-2,3-dimethyl-pyrazolone and from 0.02 to 1 mg of $SnCl_2 \cdot 2 H_2O$ with $^{88m}Tc$-pertechnetate in 1 to 10 ml of physiological saline solution.

6. A process as claimed in claim 1 or 3 wherein 1-phenyl-2,3-dimethyl-pyrazolone-4-methylamino-methylsulfonic acid or 1-phenyl-2,3-dimethyl-pyrazolone-tin-$^{99m}Tc$ compounds are in a physiological saline solution.

7. A diagnostic agent for visualizing the RES consisting essentially of a colloidal 1-phenyl-2,3-dimethyl-pyrazolone-4-methylamino-methylsulfonic acid-tin-(II)$^{99m}Tc$ compound or colloidal 1-phenyl-2,3-dimethyl-pyrazolone-tin(II)$^{99m}Tc$ compound in physiologically saline solution.

* * * * *